US00PP36286P2

(12) United States Plant Patent
Dikkenberg

(10) Patent No.: US PP36,286 P2
(45) Date of Patent: Dec. 3, 2024

(54) ***WESTRINGIA* PLANT NAMED 'WES09'**

(50) Latin Name: *Westringia fruticosa*
Varietal Denomination: WES09

(71) Applicant: Ronald Dikkenberg, Wodonga (AU)

(72) Inventor: Ronald Dikkenberg, Wodonga (AU)

( * ) Notice: Subject to any disclaimer, the term of this patent is extended or adjusted under 35 U.S.C. 154(b) by 0 days.

(21) Appl. No.: 18/445,968

(22) Filed: Apr. 19, 2024

(51) Int. Cl.
*A01H 5/02* (2018.01)
*A01H 6/70* (2018.01)

(52) U.S. Cl.
USPC ..... Plt./226

(58) Field of Classification Search
USPC ..... Plt./226
See application file for complete search history.

(56) References Cited

U.S. PATENT DOCUMENTS

PP27,898 P3 * 4/2017 Brown ..... Plt./226

* cited by examiner

*Primary Examiner* — Karen M Redden
(74) *Attorney, Agent, or Firm* — Samuel R. McCoy, Jr.

(57) ABSTRACT

'WES09' is a distinctive variety of *Westringia* plant which is characterized by the combination of a compact and decumbent growth habit, variegated foliage, an abundance of small white flowers in spring, and the stability of all characteristics from generation to generation.

2 Drawing Sheets

Latin name of the genus and species: The Latin name of the genus and species of the novel variety disclosed herein is *Westringia fruticosa.*

Variety denomination: The inventive variety of *Westringia fruticosa* disclosed herein has been given the variety denomination 'WES09'.

BACKGROUND OF THE INVENTION

Parentage: 'WES09' is a spontaneous partial-plant mutation which was discovered in 2019 growing amongst a cultivated population of *Westringia fruticosa* 'WES05' (unpatented), at a commercial plant nursery facility in Cobram East, Victoria, Australia. The mutation was first noted for its unique, variegated leaves relative to those of the parent plant and was subsequently isolated for further evaluation in order to confirm the distinctness and stability of the characteristics first observed. Upon confirmation of distinctness and stability, the new *Westringia* plant was selected for commercialization and given the name 'WES09'.

Asexual Reproduction: 'WES09' was first propagated asexually by semi-hardwood cuttings in Cobram East, Victoria, Australia in 2019 and has since been asexually propagated by vegetative cuttings through five successive generations. The distinctive characteristics of the inventive 'WES09' variety are stable from generation to generation; clones of the variety produced by asexual reproduction maintain the distinguishing characteristics of the original plant.

SUMMARY OF THE INVENTION

The cultivar 'WES09' has not been observed under all possible environmental conditions and the phenotype may vary somewhat with variations in the instant environment such as temperature, day length, and light intensity, without, however, any variance in genotype. The following traits have been repeatedly observed and represent the distinguishing characteristics of the new *Westringia* cultivar, 'WES09'.

1. *Westringia* 'WES09' exhibits a compact, densely-foliage, decumbent growth habit with a relatively short plant height; and
2. *Westringia* 'WES09' exhibits juvenile foliage that is green, generally appearing as greyed-green, and broadly margined with pale golden yellow, and strongly suffused with yellow towards the base; and
3. *Westringia* 'WES09' exhibits mature foliage that is green, generally appearing as greyed-green, and broadly margined with near-white; and
4. *Westringia* 'WES09' exhibits an abundance of small, white, solitary flowers in spring and sporadically during the summer.

BOTANICAL DESCRIPTION OF THE PLANT

Figure 1:
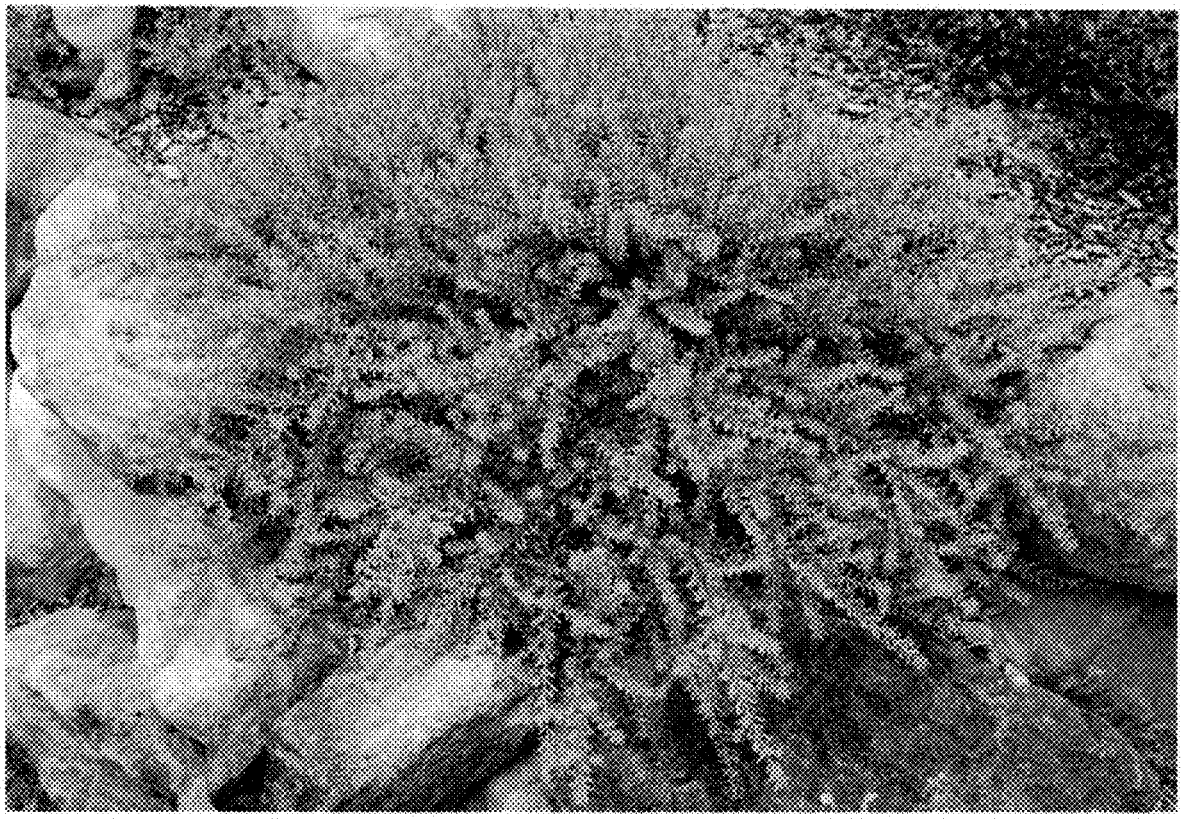
FIG. 1 shows, as nearly true as it is reasonably possible to make the same in color illustrations of this type, an exemplary 'WES09' plant. The plant shown is approximately 24 months old, planted in the ground, in Clarendon, New South Wales, Australia.
Figure 2:
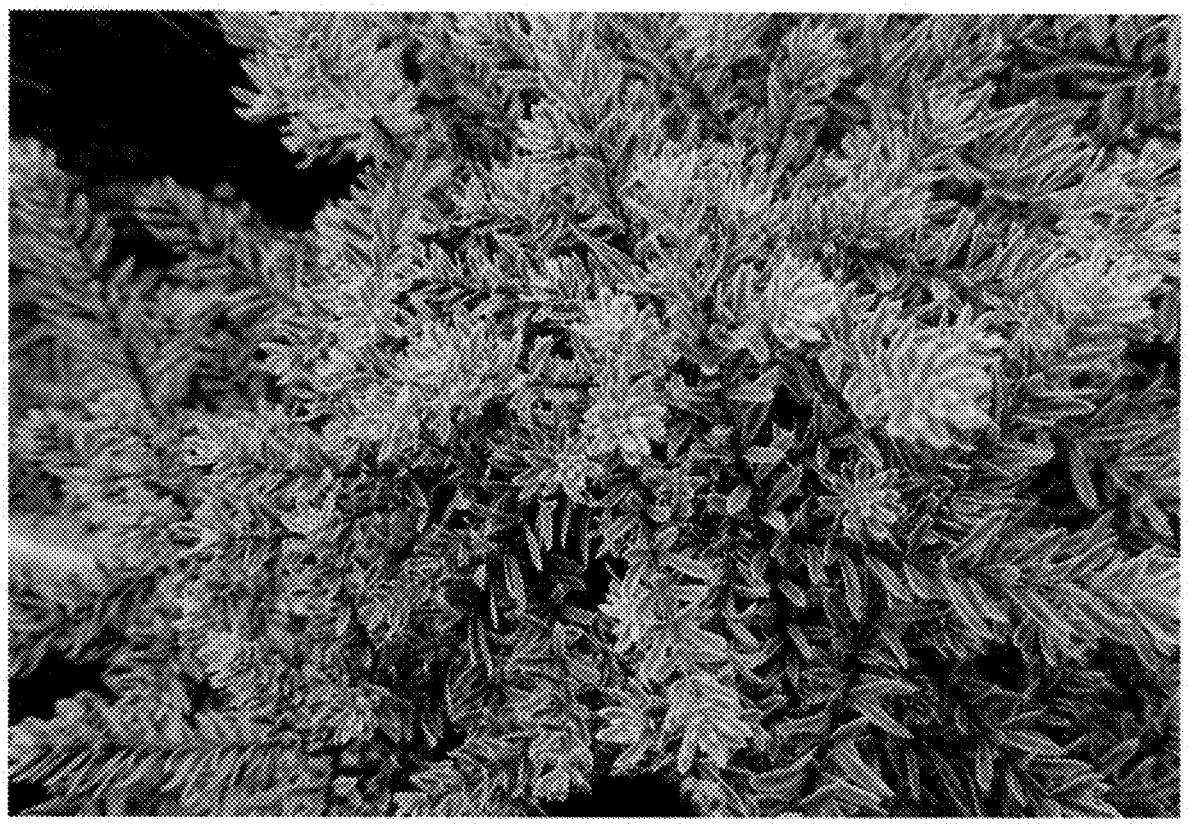
FIG. 2 shows, as nearly true as it is reasonably possible to make the same in color illustrations of this type, the typical juvenile and mature foliage of 'WES09'.

The following is a detailed botanical description of a new and distinct variety of a *Westringia fruticosa* plant known as 'WES09'. Unless indicated otherwise, the descriptions disclosed herein are based upon observations made in March of 2024 from a 24-month-old 'WES09' plant, established in a full-sun landscape in Clarendon, New South Wales, Australia. The observed plant was maintained with granular slow-release fertilizer and regularly watered with overhead irrigation. No pest and disease measures were taken.

Those skilled in the art will appreciate that certain characteristics will vary with older or, conversely, younger plants. 'WES09' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 1986 edition.

General plant description:

*Plant habit*.—Decumbent, densely-foliaged growth habit.

*Vigor*.—Vigorous.

*Growth rate*.—Fast-growing.

*Height*.—42 cm.

*Width*.—65 cm.

*Bloom period*.—Spring and sporadically at other times of year, depending on climate.

*Hardiness*.—USDA Zone 9 to 11.

*Propagation*.—Method — Propagation is accomplished using semi-hard wood cuttings. Roots well without rooting compound or hormone. Time to develop roots — Approximately 21 days at 20 degrees Celsius. Crop time-From approximately six to eight months are needed to produce a well rooted 14 cm nursery pot, starting from a rooted cutting. Crop time varies with location and production practices.

*Pest and disease susceptibility or resistance*.—Not any more or less susceptible to pests or diseases known to affect *Westringia fruticosa*.

*Cultural tolerances*.—*Westringia* is commonly known to perform well in sandy soils, but also tolerates heavy, clay-type soils well. 'WES09' can also be grown in a relatively wide pH range and is also tolerant of above-normal salt concentration in the soil environment and is also tolerant of aerosol salt exposure. 'WES09' has good drought tolerance, once established.

Roots: The roots of 'WES09' are colored white, nearest to RHS 155D, fleshy and thick, similar to other *Westringia* species and cultivars.

Stem:

*General habit*.—Multiple main stems; basally branched; freely branching habit.

*Attitude*.—Decumbent.

*Aspect*.—Terete, yet angular.

*Stem dimensions*.—The longest of any mature stems is approximately 35 to 38 cm in length with a diameter of 8 to 9 mm near the base.

*Internode length*.—Internodes near the plant base are 9 mm on average, while the internodes on the longest outstretching stems average 16 mm.

*Stem strength*.—Moderately strong.

*Texture*.—Juvenile stems are tomentose; mature stems are glabrous, corky and pruinose.

*Color, juvenile stems*.—Yellow-green, nearest to in between RHS 144A and 144B.

*Color, mature stems*.—Brown, nearest to in between RHS 200A and 200B, with grey-brown (RHS199D) striations at maturity.

Foliage:

*Shape*.—Narrowly elliptic.

*Division*.—Simple.

*Apex*.—Acute.

*Base*.—Cuneate.

*Margins*.—Entire.

*Arrangement*.—Whorled.

*Attachment*.—Petiolate.

*Texture, adaxial and abaxial surfaces*.—Glabrous; coriaceous.

*Luster, adaxial and abaxial surfaces*.—Matte to slightly glossy.

*Mature leaf dimensions*.—1.8 cm long and 0.45 cm wide.

*Color*.—Juvenile color, adaxial surface — Green, nearest to RHS 138B and mottled with 138C; broadly margined with green-yellow, nearest to RHS 1C; laminas are strongly suffused with green-yellow, RHS 1B, proximally. Juvenile color, abaxial surface — Green, nearest to RHS 138C and mottled with 138B; broadly margined with green-yellow, nearest to RHS 1C; laminas are strongly suffused with green-yellow, RHS 1B, proximally. Mature color, adaxial surface — Green, nearest to RHS 138B and mottled with 138C; broadly margined with white, nearest to RHS 155D. Mature color, abaxial surface — Green, nearest to RHS 138C and mottled with 138B; broadly margined with white, nearest to RHS 155D.

*Venation*.—Pattern — Reticulate but very inconspicuous. Color, adaxial surfaces — Indistinguishable from surrounding foliage. Color, abaxial surfaces — Indistinguishable from surrounding foliage.

*Petiole*.—Aspect — Flattened terete. Dimensions — Approximately 1.5 to 2.0 mm in length; diameter is approximately 1 mm. Strength — Moderately strong. Texture, adaxial and abaxial surfaces — Glabrous. Luster, adaxial and abaxial surfaces — Slightly glossy. Color, adaxial and adaxial surfaces — Greyed-orange, nearest to RHS 166A.

Inflorescence: Flowers are solitary; no inflorescence.

Flower bud:

*Shape*.—Broad oblong to obovoid.

*Length*.—6.0 mm.

*Diameter*.—3.25 mm.

*Texture*.—Smooth and glabrous.

*Luster*.—Matte.

*Color*.—Yellow-green, nearest to RHS 144B, and suffused darker, nearest to RHS 146C; emerging flower petals are green-white, nearest to RHS 157D.

Flower:

*Natural flowering season*.—The heaviest flowering occurs in spring, with sporadic flowering through summer.

*Abundance of flowers*.—Abundant.

*Shape, type*.—Labiate; sympetalous; irregular.

*Attachment*.—Sessile.

*Aspect*.—Upright to outward.

*Flower longevity on plant*.—Approximately five days.

*Persistent or self-cleaning*.—Self-cleaning.

*Fragrance*.—Non-fragrant.

*Diameter*.—1.45 cm.

*Depth*.—2.1 cm.

*Pedicels*.—None; flowers are sessile.

*Calyx*.—Shape — Campanulate with sepals fused into a bell shape, with free sepal lobes. Length — 0.85 cm. Diameter — 0.8 cm. Sepals — Quantity — 5 fused sepals, with free sepal lobes. Shape of the lobes — Deltoid. Lobe dimensions — 0.4 cm long and 0.45 cm wide. Apex — Acute. Base — Fused. Sepal reflex — Not reflexed. Margin — Entire. Texture, upper surface — Smooth and lightly tomentose. Texture, lower surface — Smooth and lightly tomentose. Luster, upper surface — Very slightly glossy. Luster, lower surface — Very slightly glossy. Color — Inner surface — Yellow-green, nearest to in between RHS 144A and 146B. Outer surface — Yellow-green, nearest to in between RHS 144A and 146B.

*Petals*.—Quantity — 5 petals; two upper petals fused into a large lobe and three lower petals with free lobes. Shape — The petal lobes are spatulate. Apex — Variable; broad emarginate to retuse and truncate. Base — Fused, forming a floral tube. Margin — Entire; ciliate; moderate undulation. Texture, upper surface — Tomentose. Texture, lower surface — Tomentose. Petal and floral tube color — When opening, inner surface — White, nearest to RHS 155D. When opening, outer surface — White, nearest to RHS 155D. Fully opened, inner surface — The floral tube and petal lobes are white, nearest to RHS 155D, with small violet spots at the throat of the floral tube, nearest to RHS 84B. Flower color does not fade with age. Fully opened, outer surface — The floral tube and petal lobes are white, nearest to RHS 155D. Flower color does not fade with age. Petal venation color — Fully opened, upper surface — White, nearest to RHS 155D. Fully opened, lower surface — White, nearest to RHS 155D.

Reproductive organs:

*Androecium*.—Stamens — Quantity — Approximately 4. Anthers — Attachment — Dorsifixed. Shape — Oblong with longitudinal dehiscence. Dimensions — 0.25 cm long and 0.1 cm wide. Color — White, nearest to RHS 155A. Filaments — Dimensions — 0.7 cm long and approximately 0.1 cm in diameter. Color — White, nearest to RHS 155A. Amount of Pollen — Sparse. Pollen color — Greyed-yellow, RHS 165B.

*Gynoecium*.—Pistil — Quantity — 1. Length — 0.5 cm. Style — Dimensions — 0.6 cm long and approximately 0.1 cm in diameter. Color — White, nearest to RHS 155A. Stigma — Shape — Globose. Length — 0.1 cm. Diameter — 0.125 cm. Color — White, nearest to RHS 155A.

Fruit and seed: Not observed.

COMPARISON WITH THE PARENT

Plants of the new cultivar 'WES09' are similar to the parent, *Westringia fruticosa* 'WES05' (not patented), in most horticultural characteristics. However, 'WES09' exhibits variegated foliage whereas 'WES05' exhibits foliage that is absent of variegation. Furthermore, the base foliage color of 'WES09' is green though generally appearing as greyed-green, whereas the base foliage color of 'WES05' is dark green.

COMPARISON WITH THE MOST SIMILAR VARIETIES KNOWN TO THE INVENTOR

Plants of the new cultivar 'WES09' are comparable to the commercial varieties *Westringia fruticosa* 'Smokey' (not patented) and *Westringia fruticosa* 'Morning Light' (not patented) in that all three varieties exhibit variegated foliage. However, 'WES09' exhibits a shorter plant height and decumbent growth habit compared to 'Smokey' and 'Morning Light' which both exhibit taller plant heights and upright, rotund growth habits. Also, the flowers of 'WES09' are generally white whereas the flowers of 'Smokey' are white and lightly suffused with violet, and the foliage of 'Smokey' is more narrowly margined with white. 'Morning Light' exhibits foliage with a base color that is a light shade of greyed-green whereas the base foliage color of 'WES09' is green, though generally appearing as a darker shade of greyed-green relative to 'Morning Light'.

That which is claimed is:

1. A new and distinct variety of *Westringia fruticosa* plant named 'WES09', substantially as described and illustrated herein.

* * * * *